US007198908B2

(12) United States Patent
Ochi et al.

(10) Patent No.: US 7,198,908 B2
(45) Date of Patent: Apr. 3, 2007

(54) METHOD FOR MEASURING STIFFNESS OF A CULTURED TISSUE, USING A STIFFNESS MEASUREMENT DEVICE HAVING A VIBRATION DETECTIVE UNIT

(75) Inventors: Mitsuo Ochi, 2-11-3, Yamamoto, Asaminami-ku, Hiroshima-shi, Hiroshima, 731-0137 (JP); Junji Iwasa, Shimane (JP); Masatoshi Tobita, Shimane (JP); Masakazu Katoh, Aichi (JP); Takeyuki Yamamoto, Aichi (JP); Rika Fukushima, Aichi (JP); Toyokazu Kurushima, Aichi (JP)

(73) Assignees: Mitsuo Ochi, Hiroshima (JP); Japan Tissue Engineering Co., Ltd., Aichi (JP)

( * ) Notice: Subject to any disclaimer, the term of this patent is extended or adjusted under 35 U.S.C. 154(b) by 18 days.

(21) Appl. No.: 10/921,339

(22) Filed: Aug. 19, 2004

(65) Prior Publication Data

US 2005/0019748 A1    Jan. 27, 2005

Related U.S. Application Data

(60) Division of application No. 10/083,583, filed on Feb. 27, 2002, now Pat. No. 6,815,179, which is a continuation-in-part of application No. 09/934,581, filed on Aug. 23, 2001, now abandoned.

(30) Foreign Application Priority Data

Feb. 20, 2001   (JP) ............................. 2001-043935
Jan. 22, 2002   (JP) ............................. 2002-012628

(51) Int. Cl.
   *C12P 1/00*   (2006.01)
(52) U.S. Cl. ........................ 435/41; 435/325; 435/375; 435/395
(58) Field of Classification Search .................. 435/41, 435/29, 72, 287.1, 325, 373–5, 395, 402
See application file for complete search history.

(56) References Cited

U.S. PATENT DOCUMENTS

| 5,700,688 | A | 12/1997 | Lee et al. | |
| 6,068,604 | A | 5/2000 | Krause et al. | |
| 6,815,179 | B2* | 11/2004 | Ochi et al. | ..................... 435/41 |
| 2003/0100824 | A1* | 5/2003 | Warren et al. | ............... 600/407 |
| 2005/0112759 | A1* | 5/2005 | Radisic et al. | ............... 435/366 |
| 2005/0249667 | A1* | 11/2005 | Tuszynski et al. | ............ 424/9.3 |

FOREIGN PATENT DOCUMENTS

| EP | 0 764 842 A2 | 3/1997 |
| WO | WO 98/08073 A1 | 2/1998 |

OTHER PUBLICATIONS

Chondrocytes in agarose culture synthesize a mechanically functional extracellular matrix; Journal of Orthopaedic Research vol. 10, No. 6, 1992, pp. 745-758, XP008025260 ISSN: 0736-0266 by Buschmann Michael D. et al.

"New Tactile Sensor Like The Human Hand and Its Applications" Sensors and Actuators A, Elsevier Sequoia S. A. Lausanne, Ch, vol. A35, No. 1, Oct. 1, 1992, pp. 9-15, XP000312352 ISSN: 0924-4247, p. 11; figure 2 by Sadao Omaia et al.

"Vibrotactile palpation instrument for use in minimal invasive surgery" Engineers in Medicine and Biology Society, 1996. Bridging Disciplines for Biomedicine, 18th Annual International Conference of the IEEE Amsterdam, Netherlands Oct. 31-Nov. 3, 1996, New York, NY, USA, IEEE, US Oct. 31, 1996 pp. 179-180, XP010262509 ISBN: 0-7803-3811-1; pp. 179 figure 1 by Petter E. et al.

*Development of Micro Tactile Sensor for Detecting Stiffness of Cell Using Piezoelectric Element and Applications*, Technical Digest of the 14th Sensor Symposium 1996.

*Measurement of Elastic Properties of Ovum Cell Using New Tactile Sensor*, Technical Digest of the 15th Sensor Symposium 1997.

*New Tactile Sensor Like the Human Hand and its Applications*, Sensors and Actuators A, 1992.

*A New Type of Tactile Sensor For Detecting the Hardness of Objects Like the Human Hand*, Tissue Engineering 1989.

*New Tactile Senor for Sensing Hardness Like the Human Hand and Its Applications for Living*, Tissue Technical Digest of the 9th Sensor Symposium 19990.

[2-PE-10] *Changes in Stiffness of Gel With Embedding of a Chrondrocyte, Transplanted to Injury Model of the Epiphyseal Plate Proximal* to the Tibia (partially translated). J. jpn. Orthop. Assoc. 74(8) 2000.

[2-E-22] *Culture Methods for Mixture of Chrondrocytes and Mesenchymal Stem Cells Embedded in Atelocollegen Gel*, J. Jpn. Othro. Assoc. 74(8), 2000.

* cited by examiner

*Primary Examiner*—Ralph Gitomer
(74) *Attorney, Agent, or Firm*—Sughrue Mion, PLLC (57) ABSTRACT

To determine the transplant compatibility of an in vitro cultured tissue, a method measures the stiffness of the cultured tissue by using a stiffness measuring device, which stiffness measuring device includes a detecting unit and calculation means, the detecting unit includes a contact unit, a vibrator connected to the contact unit, and a vibration detecting unit for detecting the vibration of the vibrator, and the calculation means determines stiffness information by calculation based on the detected result from the vibration detecting element; and by bringing the contact unit into contact with the cultured tissue. With this method the transplant compatibility of the cultured tissue can be non-destructively and easily determined easily and the quality of the cultured tissue can be appropriately controlled.

6 Claims, 5 Drawing Sheets

Change in Stiffness with Time

Fig. 8

Change in Frequency Plotted Against Displacement

US 7,198,908 B2

METHOD FOR MEASURING STIFFNESS OF A CULTURED TISSUE, USING A STIFFNESS MEASUREMENT DEVICE HAVING A VIBRATION DETECTIVE UNIT

This is a divisional of application Ser. No. 10/083,583 filed Feb. 27, 2002, now U.S. Pat. No. 6,815,179 which is a Continuation-in-part of U.S. application Ser. No. 09/934,581 filed Aug. 23, 2001 (now abandoned). The entire disclosures of the prior applications, application Ser. No. 10/083,583 is considered part of the disclosure of the accompanying Divisional application and is hereby incorporated by reference.

BACKGROUND OF THE INVENTION

1. Field of the Invention

The present invention relates to a method of measuring the stiffness of an in vitro cultured tissue for determining the transplant compatibility of the cultured tissue, a method of determining the transplant compatibility of the cultured tissue, a quality-control method for the cultured tissue, and a method of preparing a transplant-compatible cultured tissue.

2. Description of the Related Art

Regeneration medicine and tissue engineering, in which cells are seeded and cultured in vitro on a tissue regeneration scaffold (base material or support medium) and a tissue is regenerated to thereby reconstruct a human tissue, and the reconstructed cultured tissue is applied onto a living human body to thereby treat the living body have received attention in recent years. Such cultured tissue for transplantation must be examined for compatibility (suitability) for transplantation upon the application to the living body or must be examined for suitability for shipment upon shipment from a supplier.

As a possible candidate for methods for the determination of transplant compatibility, for the successive determination of the culture conditions or for the determination upon shipment (offering), a method of observing the structure of a cultured tissue is known, in which part of the cultured tissue is cut to thereby prepare tissue cross-sections, a produced matrix is stained with a stain, and the resulting chromatic figure is observed under a microscope.

However, it takes a long time to prepare tissue cross-sections for examination and such microscopic observation requires great effort from, and places a load on the examiner. Additionally, in order to obtain chromatic figures for each observation, this method requires a large quantity of test tissue pieces overall since part of the cultured tissue must be cut to prepare test tissue pieces, other cultured tissue (cultured tissue pieces of the same lot) must be cultured in the same conditions, etc.

Alternatively, an attempt has been made to verify the relationship between the amount of a produced matrix and the stiffness of the cultured tissue by a method of measuring the stiffness of the cultured tissue, in which the cultured tissue is processed with, for example, a cork borer and is subjected to a destruction test such as a compression test. Such a destruction test requires, however, a large quantity of tissue test specimens as in the observation of chromatic figures, since the destruction method requires the tissue test specimens of another cultured tissue of the same lot.

In addition, cell growth depends on the age or other conditions of a cell provider (cell donor) or on the nature of individual cells, and the degree of growth subtly varies from one cultured tissue to another, and therefore it is difficult to predict, for example, the time needed to become a culture tissue suitable for transplantation. For example, the time when the cultured tissue becomes compatible for transplantation cannot be significantly predicted. The difficulty in prediction of the culture inhibits precise culture control for bringing the cultured tissue into a desired condition. For these reasons, the quality of the cultured tissue upon provision cannot be significantly stabilized and a transplant-compatible cultured tissue cannot be reliably and easily prepared.

SUMMARY OF THE INVENTION

Under these circumstances, an object of the present invention is to provide methods of measuring the stiffness of a cultured tissue and of determining the transplant compatibility of the cultured tissue, in order to easily and nondestructively determine the transplant compatibility of the cultured tissue, to provide a quality-control method that can easily and appropriately control the quality of a cultured tissue, and to provide a method for reliably and easily preparing a transplant-compatible cultured tissue.

Specifically, the present invention provides, in one aspect, a method of measuring the stiffness of a cultured tissue for the determination of the transplant compatibility of the cultured tissue being cultured in vitro, which method is carried out by using a stiffness measuring device, the stiffness measuring device includes a detecting unit and calculation means, the detecting unit includes a contact unit, a vibrator connected to the contact unit, a vibration detecting unit for detecting vibration of the vibrator, where the calculation means determines stiffness information by calculation based on the detected result from the vibration detecting unit, and which method includes the steps of: bringing the contact unit into contact with the cultured tissue and measuring the stiffness of the cultured tissue.

According to the method of measuring the stiffness, the stiffness information of the cultured tissue is obtained from a change in frequency of the vibrator when the contact unit is contacted with the cultured tissue, and the stiffness of the cultured tissue is calculated from the stiffness information to thereby determine the amount of a matrix produced by the cultured tissue or to thereby determine the transplant compatibility based on the amount of the produced matrix.

Preferably, the detecting unit in the aforementioned method further includes a load detecting unit for detecting a load applied onto the contact unit, and the stiffness of the cultured tissue is measured based on a relationship between the vibration of the vibrator detected by the vibration detecting unit and the load detected by the load detecting unit.

According to this configuration, information of the load applied onto the contact unit is obtained, and the stiffness of the cultured tissue can be measured based on a relationship between the load information and the vibration of the vibrator to thereby further appropriately determine the transplant compatibility of the cultured tissue.

The detecting unit for use in the stiffness measuring method preferably further includes a displacement detecting unit for detecting a displacement of the contact unit from a reference position, and the stiffness of the cultured tissue is measured based on a relationship between the vibration of the vibrator detected by the vibration detecting unit and the displacement detected by the displacement detecting unit.

According to this embodiment, the contact unit is displaced from the reference position to yield a displacement, and the stiffness of the cultured tissue can be measured based on a relationship between the displacement and the vibration of the vibrator to thereby further properly determine the transplant compatibility of the cultured tissue based on its stiffness.

The cultured tissue for use in the measuring method preferably includes at least one of a cell and a matrix produced by the cell, which cell is seeded and cultured on a tissue regeneration scaffold having a three-dimensional structure, wherein the stiffness of the tissue regeneration scaffold alone on which no cell is seeded or the stiffness of the cultured tissue immediately after the seeding of the cell is previously measured and the resulting stiffness is defined as reference stiffness information, and the reference stiffness information is compared with the stiffness information of the cultured tissue.

According to this embodiment, the stiffness of the cultured tissue is measured by comparing the reference stiffness information with the stiffness information of the cultured tissue, which reference stiffness information is stiffness information of the tissue regeneration scaffold alone on which no cell is seeded. Alternatively, the stiffness information of the cultured tissue immediately after cell seeding can be used instead of the stiffness information of the tissue regeneration scaffold alone. This configuration can further appropriately determine the transplant compatibility of the cultured tissue based on its stiffness by comparing the same with the stiffness information of the tissue regeneration scaffold.

The tissue regeneration scaffold in the measuring method may include one selected from among collagen, gelatin, hyaluronic acid, fibronectin, fibrin, chitin, chitosan, laminin, dermatan sulfate, heparan sulfate, chondroitin sulfate, calcium alginate, calcium phosphate, calcium carbonate, polyglycolic acid, polylactic acid, and polyrotaxane.

The cell origin of the cultured tissue may be at least one selected from among chondrocyte, osteoblasts, fibroblasts, endothelial cells, epithelial cells, myoblasts, adipocytes, hepatic cells, nerve cells, and progenitor cells of these cells.

In another aspect, the present invention provides a method of determining the transplant compatibility of a cultured tissue cultured in vitro, which method uses the aforementioned method of measuring the stiffness of the cultured tissue.

This method determines the transplant compatibility of the cultured tissue using the aforementioned method of measuring the stiffness. This method can therefore objectively and appropriately determine the transplant compatibility of the cultured tissue based on the measured stiffness without destruction of the cultured tissue.

The present invention provides, in a further aspect, a method for the quality control of a cultured tissue, which method includes the steps of measuring the stiffness of an in vitro cultured tissue at a predetermined time after the initiation of cultivation, predicting a change in stiffness of the cultured tissue with time after measurement, and controlling culture conditions of the cultured tissue based on the resulting prediction.

The quality control method for a cultured tissue controls the culture conditions based on the predicted change in stiffness of the cultured tissue with time to thereby cultivate the cultured tissue. This method can therefore easily and appropriately control the quality of the cultured tissue based on a specific indicator, a change in stiffness.

In the quality control method, the stiffness of the cultured tissue is preferably measured using a stiffness measuring device, the stiffness measuring device includes a detecting unit and calculation means, and the detecting unit includes a contact unit, a vibrator connected to the contact unit, and a vibration detecting unit for detecting the vibration of the vibrator, and a calculation means determines stiffness information by a calculation based on the detection result from the vibration detecting unit.

In this quality control method, the stiffness of the cultured tissue is measured by using the stiffness measuring device used in the stiffness measuring method, to thereby predict a change in stiffness of the cultured tissue with time. Therefore, this embodiment can easily and appropriately control the quality of the cultured tissue itself in a nondestructive manner, the stiffness of which has been measured.

In addition and advantageously, the present invention provides a method of preparing a transplant-compatible cultured tissue, which method includes the step of measuring the stiffness of a cultured tissue cultured in vitro at a predetermined time after the initiation of cultivation to determine the transplant compatibility of the cultured tissue.

In the method of preparing a cultured tissue, the tissue is cultured while measuring its stiffness, and the cultured tissue can be cultured while determining its transplant compatibility based on the stiffness of the cultured tissue as an indicator, to thereby reliably prepare a transplant-compatible cultured tissue.

In the preparation method, preferably, the change in stiffness of the cultured tissue with time after measurement is predicted based on the measurement of stiffness of the cultured tissue, and the culture conditions of the cultured tissue are controlled to thereby prepare the transplant-compatible cultured tissue.

In this method a cultured tissue is prepared under culture conditions appropriately controlled based on the stiffness of the cultured tissue, and therefore a transplant-compatible cultured tissue can be easily and reliably prepared under appropriately controlled culture conditions.

DESCRIPTION OF THE PREFERRED EMBODIMENTS

Figure 1:
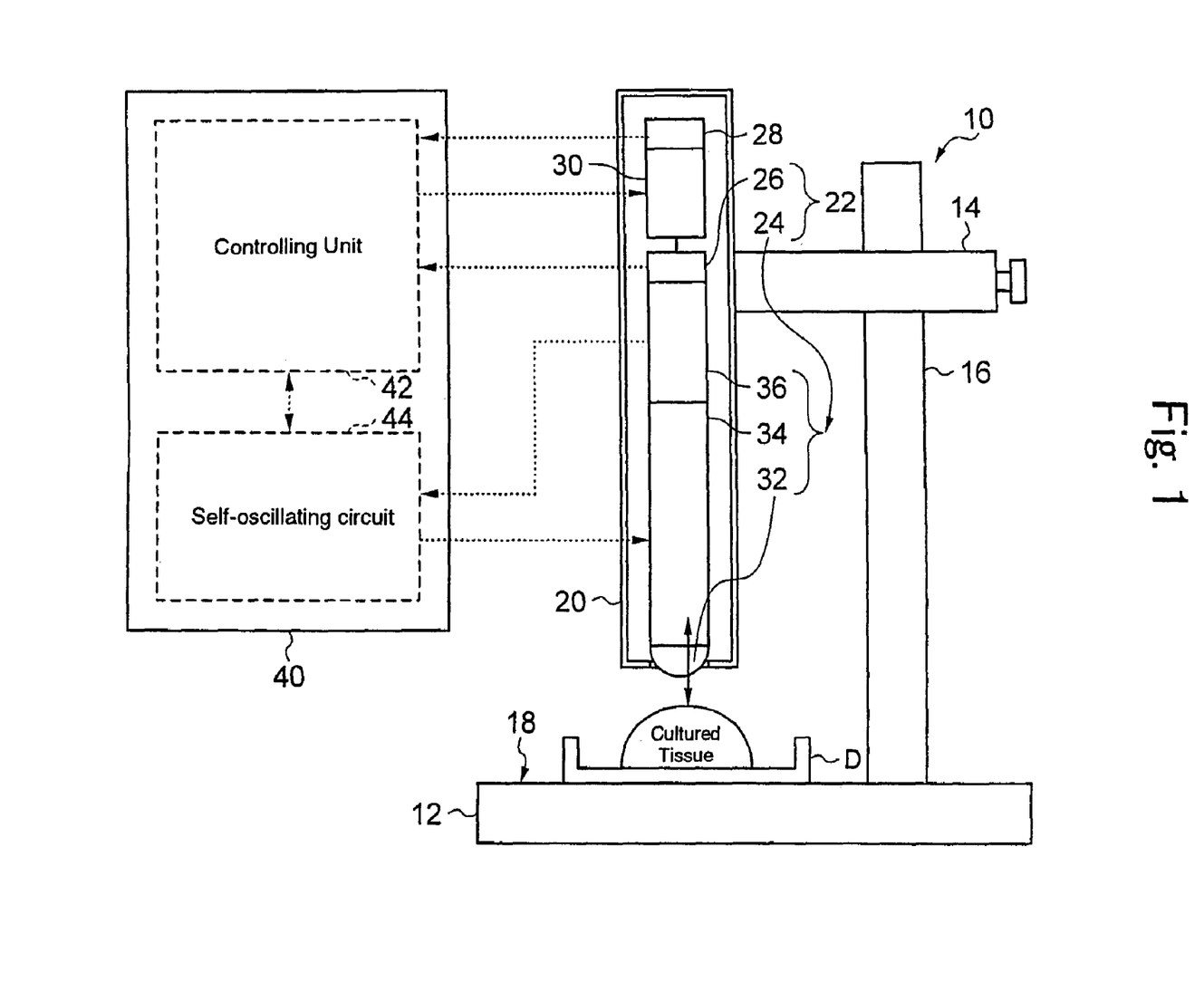
FIG. 1 is a diagram showing an embodiment of a stiffness measuring device for use in the present invention.

With reference to FIG. 1, stiffness measuring device 10 for use in the present invention will be illustrated in detail below.

Stiffness measuring device 10 comprises probe 20 (corresponding to the detecting unit according to the invention)

and control unit 40 (corresponding to the calculation means according to the invention). Probe 20 is fixed to and held by stand 12, and control unit 40 controls driving of each unit of probe 20 and manipulates a signal detected from each sensor of probe 20.

Probe 20 houses measuring element 22 and motor 30, the measuring element 22 is composed of tactile sensor unit 24 and pressure sensor unit 26, and the motor 30 drives measuring element 22 upward and downward. Displacement sensor unit 28 is integrally fixed to motor 30 and detects the travel of measuring element 22 based on the number of revolutions of the drive shaft of motor 30. Motor 30 is fixed to probe 20 and drives measuring element 22 upward and downward, measuring element 22 being arranged to be vertically movable in probe 20.

Tactile sensor unit 24 is composed of integrally coupled contact 32, vibrator 34 and pickup 36. Contact 32 is of a hemispherical shape and is arranged at the tip of measuring element 22. The diameter of contact 32 can appropriately be set depending on the size and type of cultured tissue and on the method for measurement. Vibrator 34 is composed of a piezoelectric element, and pickup 36 is composed of a vibration detecting piezoelectric element, for example.

Pressure sensor unit 26 includes a pressure sensor composed of, for example, a pressure sensing element. The pressure sensor is fixed to pickup 36 of tactile sensor unit 24 and detects a load applied onto contact 32. The pressure sensor is fixed to pickup 36 in such a manner that its natural frequency does not affect the frequency detection in pickup 36.

Displacement sensor unit 28 includes a displacement sensor composed of, for example, an encoder and potentiometer. The displacement sensor detects the displacement in position based on the travel of measuring element 22 when it is driven by motor 30 arranged in probe 20 and moves upward and downward in FIG. 1.

Probe 20 is movably arranged with respect to stand 12 via arm 14 and supporting shaft 16. Stand 12 includes stage 18 that faces contact 32 arranged at the lower end of probe 20. A cultured tissue to be measured is placed on stage 18.

Control unit 40 is composed of controlling unit 42 and self-oscillating circuit 44, and a computer (not shown) is connected to control unit 40.

Self-oscillating circuit 44 is composed of an amplifying circuit and a band pass filter (neither of them shown) and is connected to vibrator 34 and pickup 36. Additionally, self-oscillating circuit 44 has a circuitry in which a signal output from pickup 36 is amplified in the amplifying circuit and is allowed to pass through the band pass filter and is forcedly fed back to vibrator 34. By this configuration, the degree of amplification of the amplifying circuit and the characteristics of the band pass filter are adjusted, and a phase difference between the input and output of self-oscillating circuit 44 is adjusted to zero and vibrator 34 is allowed to vibrate to thereby self-oscillate.

Controlling unit 42 is connected to self-oscillating circuit 44 and controls the vibration of vibrator 34 in tactile sensor unit 24 in such a manner that the frequency characteristic of the band pass filter corresponds to the frequency characteristic of vibrator 34, to thereby calculate the stiffness information.

Controlling unit 42 is connected to pressure sensor unit 26 and to displacement sensor unit 28, respectively, and calculates load information and displacement information respectively from the load detected by pressure sensor unit 26 and the displacement detected by displacement sensor unit 28.

The displacement information is calculated based on positional information from displacement sensor unit 28. In the present embodiment, any position is defined as an initial position, and the initial position is defined as a reference position in the positional information. Then, the reference position is defined as zero and travel upon the downward movement of measuring element 22 driven by motor 30 is defined as positive, and the positional information obtained in this procedure is defined as the displacement information.

Alternatively, distance between the initial position of measuring element 22 and the position at which measuring element 22 is brought into contact with the cultured tissue is defined as an idle distance, and the travel of measuring element 22 after contact with the cultured tissue is defined as the displacement information. In this case, a position at which measuring element 22 comes in contact with the surface of the cultured tissue as detected based on the pressure information from pressure sensor unit 26, and the difference between the reference position and the travel as determined by displacement sensor unit 28, is defined as the reference position. As another alternative, the position where the two members come into contact with each other may be determined based on the tactile information from the tactile sensor unit 24 instead of the pressure information from the pressure sensor unit 26.

When the natural frequency of the pressure sensor of pressure sensor unit 26 affects the frequency detection in pickup 36, the natural frequency of the pressure sensor may be calibrated to thereby detect a precise change in frequency.

In the computer (not shown in the figure) connected to control unit 40, an operator may set a variety of measuring conditions. Measuring condition items to be set include moving velocity (e.g., from 1 to 4 mm/s) and travel (e.g., from 1 to 10 mm) of measuring element 22. The computer controls the movement of measuring element 22 driven by motor 30, through control unit 40 based on these set conditions. Information detected by each sensor unit is transmitted to controlling unit 42, and is recorded in synchronism in a memory unit not shown.

Stiffness measuring device 10 measures the stiffness of an in vitro cultured tissue. Such cultured tissues to be measured can be any tissues that are cultured in vitro and the stiffness thereof can be measured by stiffness measuring device 10, as far as the stiffness or elasticity thereof changes with the passage of culture period. Such cells contained in such cultured tissues include, for example, chondrocytes, osteoblasts, fibroblasts, endothelial cells, epithelial cells, myoblasts, adipocytes, hepatic cells, nerve cells, and progenitor cells of these cells.

The cultured tissue does not necessarily contain a tissue regeneration scaffold, as far as a sufficient structure as a cultured tissue can be maintained. However, the cultured tissue to be measured preferably comprises a tissue regeneration scaffold having a three-dimensional structure, and at least one of a cell and a produced matrix held by the tissue regeneration scaffold. This type of cultured tissue is suitable for transplantation to living bodies as intact and its stiffness can be more properly measured using stiffness measuring device 10. From the viewpoints of construction of cultured tissue at the transplantation form and easiness in measurement, preferred cultured tissues to be determined in transplant compatibility according to the present invention include chondrocytes, osteoblasts or progenitor cells of these cells.

Tissue regeneration scaffolds for use in the present invention include, but are not limited to, collagen, gelatin, hyaluronic acid, fibronectin, fibrin, chitin, chitosan, laminin, dermatan sulfate, heparan sulfate, chondroitin sulfate, calcium alginate, calcium phosphate, calcium carbonate, polyglycolic acid, polylactic acid, and polyrotaxane. Among them, collagen, gelatin, hyaluronic acid, and fibrin are more preferred, from the viewpoints of biocompatibility and bioabsorptivity.

When the stiffness of a cultured tissue is measured by stiffness measuring device 10, culture dish D including the cultured tissue to be measured is placed on stage 18 on stand 12. In this procedure, the surface area of the cultured tissue is preferably greater than that of contact 32, and the thickness of the cultured tissue is preferably greater than a depth in measurement at which the characteristic of the cultured tissue is obtained, in order to further precisely measure the stiffness by stiffness measuring device 10. The surface area of contact 32 and the depth in measurement can be varied depending on the size of contact 32. When the size of the cultured tissue is greater than that of contact 32 and the stiffness can be measured at plural points on the cultured tissue, the stiffness is preferably measured at plural points in order to more precisely or appropriately measure the stiffness. In this connection, when the cultured tissue has constant configuration, the resulting measurements are stabilized to thereby further appropriately measure the matrix production or determine the transplant compatibility.

To further precisely or appropriately measure the stiffness, it is also preferred to change the size of contact 32 instead of, or in addition to, changing the size of the cultured tissue or increasing the number of the points of measurement. Although dependent on the size of the cultured tissue, when the area of the contact 32 to come in contact with the cultured tissue is set relatively large, stiffness information corresponding to the stiffness of the entire cultured tissue can be obtained. In contrast, when the size of contact 32 is decreased and the number of points of measurement is increased, local stiffness of the cultured tissue can be measured, and the stiffness can be precisely measured with good reproducibility by calculating the average of measurements. In view of these points, the contact area of contact 32 is preferably in a range of from equal to about one fifth the projected area of the cultured tissue in order to obtain the stiffness information corresponding to the entire cultured tissue. It is preferably one fifth or less of the projected area of the cultured tissue for obtaining the local stiffness information of the cultured tissue. To precisely measure with good reproducibility, the stiffness is preferably measured at 5 to 50 points per cultured tissue.

Next, the operation of stiffness measuring device 10 will be illustrated in detail below.

A cultured tissue to be measured is placed on stage 18, and arm 14 and supporting shaft 16 are adjusted to thereby locate probe 20 above the cultured tissue. The moving velocity and travel of measuring element 22 are set and the measurement is started.

Upon the initiation of the measurement, motor 30 starts driving and vibrator 34 starts vibrating, and measuring element 22 moves toward the cultured tissue at the predetermined moving velocity to thereby bring contact 32 of measuring element 22 into contact with the cultured tissue. The contact of contact 32 with the cultured tissue makes the oscillation frequency of vibrator 34 to change. Even after the contact with the cultured tissue, measuring element 22 moves at the predetermined moving velocity. When measuring element 22 moves predetermined distance from the reference position, controlling unit 42 gives instructions to motor 30 to reverse the direction of its rotation. Upon reversal in direction of rotation of motor 30, measuring element 22 moves upward, and contact 32 separates from the cultured tissue and returns to the reference position, thus completing the measurement.

The stiffness is measured by the series of operations based, for example, on measured values, changes, relationship of one or plural sensors among signals obtained in synchronism with the up-and-down movements of measuring element 22 and outputted from tactile sensor unit 24, pressure sensor unit 26 and displacement sensor unit 28.

Stiffness measuring device 10 acts on the operating principle that, when contact 32 in natural frequency is brought into contact with an object to be measured, the frequency of contact 32 changes upon touching the object. The stiffness of the object can be measured as stiffness information by subjecting the change in frequency to a predetermined computation. Details of such stiffness measuring devices are disclosed in, for example, Japanese Patent Application Laid-open No. 9-145691 (title of the invention: FREQUENCY DEVIATION DETECTING CIRCUIT AND MEASURING APPARATUS USING SAME). The operator operates the computer to thereby set measuring conditions and other parameters, and performs measurement of the stiffness of the cultured tissue.

According to the present invention, the transplant compatibility of a cultured tissue is determined by measuring the stiffness of the cultured tissue using aforementioned stiffness measuring device 10. As stiffness measuring device 10 sterilely and nondestructively measures the stiffness, the stiffness of a cultured tissue for transplantation itself can be measured to thereby determine its transplant compatibility.

Determination of Transplant Compatibility

A method of determining the transplant compatibility of a cultured tissue according to the present invention is based on the principle that the stiffness of the cultured tissue changes with the passage of culture period. The stiffness of the cultured tissue is one of the requirements for a transplanted cultured tissue to appropriately act upon the applied region of a patient when the cultured tissue is transplanted into the patient, and is one of the requirements for the cultured tissue to be easily handled. The stiffness of the cultured tissue changes with an increasing number of cells or an increasing mount of a matrix produced by the cells in the cultured tissue, and depends on the character of the cell type constituting the cultured tissue. The amount of a produced matrix in the cultured tissue can therefore be measured based on the measurement of the stiffness of the cultured tissue. The transplant compatibility of the cultured tissue should be practically determined based on its stiffness for every type of cultured tissue, and the inventive method of determining the transplant compatibility will be described in detail below, by taking a cultured cartilage as example.

The term "the determination of transplant compatibility" as used herein means the determination of whether the cultured tissue is suitable for transplantation at the time of its transplant and also includes the determination of whether the cultured tissue is in a suitable state at a specific point of time in consideration of the time remaining until it is transplanted. For example, since the cultured tissue is shipped only a predetermined time before transplant, it is preferable to determine whether the cultured tissue is in a suitable state in consideration of the storage conditions between shipment and transplantation and other parameters. Consequently, upon shipping, as it is preferable to determine whether the cultured tissue is in a suitable state at the point of time of shipment, the present invention can also be applied to this type of determination.

The transplant compatibility of the cultured tissue is determined from a variety of stiffness information. The stiffness information is obtained from a value or a change thereof of information from a single sensor or from a relationship between a plurality of sensor information. The sensor information is obtained based on frequency information from the tactile sensor, load information from the pressure sensor, and displacement information from the displacement sensor of stiffness measuring device 10.

(1) Determination Based on Frequency Information from Tactile Sensor

The stiffness of the cultured cartilage is measured using stiffness measuring device 10 and the transplant compatibility of the cultured cartilage is determined based on whether the resulting measurement is within an appropriate range.

Specifically, a predetermined displacement or load is applied onto measuring element 22 of stiffness measuring device 10 and measuring element 22 is brought into contact with the cultured tissue (cultured cartilage), and a change in frequency $\Delta f$ is obtained from the tactile sensor. The transplant compatibility is determined based on whether $\Delta f$ is within an appropriate range as a tissue for transplantation. The appropriate range varies depending on various parameters such as the type of the cell, the type and shape of the scaffold, conditions of measurement including the diameter of the contact, and the disease to be treated. Consequently, it must be determined by performing a preliminary test of the cultured tissue.

For example, a cultured cartilage measuring model (hereinafter briefly referred to as "measuring model") is formulated in the following manner. A chondrocyte is embedded and cultured in collagen gel to thereby yield a domical or hemispherical cultured cartilage 10 mm in diameter and 3 mm in thickness. The stiffness of the cultured cartilage is then measured in such a manner that probe 20 having hemispherical $\phi$5 mm contact 32 is placed at a point about 0.5 mm above from the top of the cultured cartilage, and is provided with a travel of 2 mm (the probe is pressed downward into the top of the cultured tissue about 1.5 mm). In the above-formulated measuring model, when contact 32 is pressed downward into the top about 1.0 mm, the appropriate range of the stiffness in terms of the change in frequency $\Delta f$ is from −200 to 0 Hz and preferably from −150 to 0 Hz. If the change in frequency $\Delta f$ is less than −200 Hz, the cultured tissue has not become sufficiently stiff and is not suitable for transplantation. If it exceeds 0 Hz, the cultured tissue has become excessively stiff and will have low affinity to a living body and may possibly fall off. The term "change in frequency $\Delta f$" as used in the present embodiment means a value obtained by subtracting the specific frequency of the measuring element from the measured frequency.

Alternatively, the criteria are determined based on $\Delta f$ under a predetermined load. For example, in the measuring model, $\Delta f$ is preferably from −150 to 0 Hz and more preferably from −100 to 0 Hz under a load of 0.067 N. If $\Delta f$ is out of this range, the cultured tissue is excessively soft or stiff as above and is not suitable for transplantation.

In contrast, when the stiffness of a cultured cartilage 30 mm in diameter and 3 mm in thickness embedded in a collagen gel is measured using probe 20 having semispherical $\phi$1 mm contact 32 from above the top of the cultured cartilage, the appropriate range of the stiffness in terms of the change in frequency $\Delta f$ under a load of 0.0049 N (0.5 gf) is from −15 to 0 Hz and is preferably from −10 to 0 Hz. As thus described above, the appropriate range varies depending on conditions for measurement and the state of the cultured tissue.

(2) Determination Based on Comparing Frequency Information from Tactile Sensor

The stiffness of a cultured tissue changes approximately proportionally with the growth of cells and the amount of a produced matrix. Accordingly, the amount of the produced matrix or the transplant compatibility of the cultured tissue can be determined by previously defining a reference model.

In this case, a scaffold alone is subjected to the culture operation, without cell seeding, under the same conditions as the cultured tissue, and the resulting cultured scaffold is defined as a reference model in determination (hereinafter briefly referred to as "reference model"), and the transplant compatibility is determined by comparing the frequency information of the cultured tissue with that of the reference model. The criteria for determination of the transplant compatibility vary depending on the scaffold to be compared, cells, culture conditions, measuring conditions, and other parameters, and an appropriate range corresponding to each cultured tissue to be measured must be determined.

A predetermined load or displacement is applied onto measuring element 22 of stiffness measuring device 10 and measuring element 22 is brought into contact with the reference model to thereby previously measure a change in frequency ($\Delta f_0$). Then, a change in frequency $\Delta f$ of the cultured tissue is measured under the same conditions as that of the reference model, and the transplant compatibility of the cultured tissue is determined by comparing the measured $\Delta f$ with $\Delta f_0$ of the reference model.

In the above-mentioned measuring model, when contact 32 is pressed downward into the top about 1.5 mm, the transplant compatibility of the cultured tissue is determined as appropriate if the stiffness information ($\Delta f$) of the cultured tissue is stiffer than the stiffness information ($\Delta f_0$) of the reference model (i.e., the ratio $\Delta f/\Delta f_0$ is less than 1.0). The ratio of changes in frequency $\Delta f/\Delta f_0$ is preferably from 0 to 0.9, and more preferably from 0 to 0.7. If the ratio $\Delta f/\Delta f_0$ is out of the above range, the cultured tissue is excessively soft or stiff as above and is not suitable for transplantation.

(3) Determination Based on Relationship Between Tactile Sense and Load Information (Displacement Information)

When contact 32 is brought into contact with the cultured tissue or scaffold and then gradually undergoes displacement, a load L increases and the change in frequency $\Delta f$ changes with increasing displacement. This change can be translated into the slope in a relationship between the tactile sense and load information. The slope includes the stiffness information and can be employed as an indicator or criteria in the determination of the transplant compatibility. Alternatively, a relationship between the tactile sense and displacement information can be used instead of the relationship between the tactile sense and load information, since the two relationships show similar tendencies. The slope may be defined as the slope of a tangent under a predetermined load or at a predetermined displacement in a diagram showing the relationship between the tactile sense and load or a diagram showing the relationship between the tactile sense and displacement. Alternatively, the slope may be approximately defined as the slope of a straight line plotted between the value under the predetermined load or at the predetermined displacement and the value at the reference position.

When $\Delta f$ is plotted against a load L in the cultured cartilage measuring model as a diagram showing the relationship between the tactile sense and load, the slope of the plot between zero and a load of 0.067 N as determined by the method of least squares is preferably from −1200 to 0 Hz/N and more preferably from −800 to −300 Hz/N. If the slope falls out of this range, the cultured tissue is either excessively soft or stiff as mentioned above, and is not suitable for transplantation.

The predetermined load in determination of the slope may be any load as far as the characteristic of the cultured tissue is obtained, but measurement at such load that the measured value is affected by factors such as the culture dish (its bottom) other than the cultured tissue is not preferred.

Alternatively, the transplant compatibility can be determined based on a change in elasticity of the cultured tissue. In this case, the elasticity of the cultured tissue is determined by observation based on the relationship between the tactile sense and load information, and the transplant compatibility is determined based on the elasticity of the cultured tissue.

In the relationship between the tactile sense and load, the elasticity is observed as a difference (residual deformation) in change in frequency between forward movement and return movement (up and down movements of measuring element 22) under the same load. Upon the measurement of the reference model, a great difference is observed in change in frequency between forward and return movements under the same load. However, when the cultured tissue has an increased elasticity due to cell growth and matrix production, the residual deformation decreases. In this manner, the transplant compatibility of the cultured tissue can be determined as appropriate when the residual deformation falls within a predetermined appropriate range. Likewise, the transplant compatibility can also be determined based on the elasticity information in the relationship between the tactile sense and displacement.

Thus, the transplant compatibility of a cultured tissue for transplantation itself can be determined or examined using stiffness measuring device 10 that can nondestructively measure the stiffness, without the use of a multiplicity of other cultured tissues of the same lot. The transplant compatibility can be easily determined by examining whether the resulting measurement falls within an appropriate range.

Additionally, the predetermined reference model smoothes the way to grasp the condition of cell growth or matrix production in the cultured tissue and facilitates the performance of the cultured tissue transplant compatibility test.

Quality Control of Cultured Tissue

A quality control method for a cultured tissue according to the present invention measures the stiffness as mentioned above over time to understand the state of cultivation, thereby predicts the state of cultivation after measurement and controls the culture conditions of cultured tissue based on the prediction, to thereby control the quality of the cultured tissue.

Specifically, the stiffness of the cultured tissue changes with the growth of an seeded cell or the production of a matrix accompanied with cell growth. In addition, when the culture conditions including the density of seeding or the type of medium are changed, the cell growth or matrix production changes with time in a different manner, and the stiffness depending on these factors changes with time in a different manner. Based on this mechanism, the present quality control method obtains stiffness information of the cultured tissue during the cultivation process, and predicts a change in the state of cultured tissue afterward. Based on the resulting prediction, the method controls the culture conditions of the cultured tissue so that the cultured tissue has an appropriate stiffness as a cultured tissue for transplantation, after a lapse of a desired culture period.

The term "quality of cultured tissue" as used herein refers to how well a transplanted graft efficiently takes or the transplanted tissue efficiently regenerates in a patient. The phrase "having transplant compatibility (or being transplant-compatible)" means that the cultured tissue meets the requirements of that term.

The term "quality control of cultured tissue" as used herein means that the number of cells and/or the amount of matrix in the cultured tissue are controlled within a predetermined range in relation with the time for providing the cultured tissue, in order to provide a transplant-compatible cultured tissue. The term "quality control of cultured tissue" means that only a cultured tissue in an appropriate state is selected at a specific time. Specifically, during cultivation, it means that by understanding the culture state at the time of measurement and adjusting the culture period and other culture conditions after measurement, the state or condition of the cultured tissue is controlled so that the cultured tissue takes on an appropriate state at a specific time such as at the time of transplantation or offering (shipment). Upon shipment of the cultured tissue, "quality control of cultured tissue" means that only a cultured tissue in an appropriate state for shipment is selected in consideration of the time period between shipment and transplantation or the condition during this time period. This configuration can maintain the quality of a cultured tissue to be offered at a constant level at all times.

Such quality control operations include grasp of the state of cultured tissue during cultivation to thereby determine whether the cultured tissue is suitable for being on the market based on the grasped state of the cultured tissue, and adjustment of various factors relating to cultivation to thereby control the state of the cultured tissue, as described in detail below. The control of the culture conditions for the quality control according to the present invention does not always require a change in culture conditions. The control of the culture conditions also includes cases where cultivation is continued under the same conditions as before when a change of culture conditions is determined to be unnecessary based on the change in stiffness information with time. The adjustment of various factors relating to cultivation includes the control (e.g. extension, shortening or keeping) of the culture period, in addition to the adjustment of the type of the medium and the medium composition such as additional nutritional factors.

In order to predict the culture state, the more the stiffness is measured to include the beginning of culture, the more properly the culture state can be predicted. In this connection, timing of measurement depends on the growth rate of a cell types constituting the cultured tissue. When the culture state can be grasped to some extent from the seeding cell density or cultivating rate, the stiffness may be measured at least once after the initiation of culture. For example, in the case of a chondrocyte, the culture state can be predicted to some extent by measuring the stiffness at the 14th day into cultivation. This procedure can more easily control the quality of cultured tissue.

Preferably, the stiffness of the cultured tissue is measured by using stiffness measuring device 10 used in the determination of the transplant compatibility. By this configuration, the quality of cultured tissue can be controlled while determining the transplant compatibility thereof based on the stiffness information, without the use of an extra device.

The cultivation of cultured tissue is controlled by changing the culture conditions to accelerate or retard the cell growth. Such control operations on the cell growth rate include, for example, changing of medium composition such as addition or removal of nutritional factors, changing of the timing of replacement of culture medium, and changing of incubation temperature. These operations can accelerate or retard the cell growth or matrix production of the cultured tissue to thereby obtain a cultured tissue in an appropriate state at a desired time. In addition, control of the culture period in the following manner can also stabilize the quality of the cultured tissue. Specifically, based on the stiffness information, the culture period is extended when the cells grow slowly, is shortened when the cells grow rapidly, and is not changed and is maintained as a predetermined period when the cells grow appropriately.

For the purpose of quality control, the stiffness of the cultured tissue must be measured under such a load or at such a displacement that the cultured tissue is not destroyed. This configuration can continuously and nondestructively measure the stiffness of the same cultured tissue and can control the quality in order to provide a cultured tissue with a stable quality.

Thus, the culture state of the cultured tissue is controlled based on its stiffness information, and the quality of cultured tissue can be precisely and stably controlled without destruction of the cultured tissue. Additionally, a cultured tissue in a desired state or condition can be provided and the quality of the cultured tissue can be controlled to yield a cultured tissue with a stable quality.

The cultivation of a cultured tissue while measuring its stiffness as mentioned above can easily prepare a transplant-compatible cultured tissue. When a cultured tissue is prepared by this method, the stiffness of the cultured tissue is measured from the beginning of incubation at predetermined intervals, and the cultured tissue is cultured while grasping a change in the cultured tissue with time and determining its transplant compatibility using the stiffness as an indicator.

This configuration can avoid insufficient culture prior to an appropriate state for transplantation or over-growth exceeding the appropriate state, since the transplant compatibility of the cultured tissue is determined during cultivation over time, using its stiffness as an indicator. By using the aforementioned stiffness measuring device 10 transplant-compatible cultured tissue can be nondestructively prepared, so numerous transplant-compatible cultured tissues can be efficiently prepared from the cultured tissue for transplantation.

By combining the above procedure with the adjustment of culture conditions described in the quality control method transplant-compatible cultured tissue can be efficiently prepared in appropriate amounts in an appropriate amount of time.

The change in frequency $\Delta f$ obtained from tactile sensor unit 24 is used as the stiffness information in the above description. Alternatively, stiffness S calculated from the change in frequency $\Delta f$ can be used in measurement of matrix production or determination of the transplant compatibility in the same manner as the change in frequency $\Delta f$. The stiffness S can be calculated according to the following equation (1):

$$\Delta f = a * \log S + b$$

wherein a and b are each a constant determined in each device.

As thus described above, the relationship between $\Delta f$ and the stiffness S varies depending on the constants differing from one device to another, and the measured $\Delta f$ easily varies depending on different configurations, diameters, and material of the probe even when the same cultured tissue is to be measured. The appropriate ranges of $\Delta f$ mentioned in relation to the embodiments of the present invention are determined based on the examples below and are not intended to limit the scope of the present invention.

EXAMPLES

The invented methods for examination of a cultured tissue based on stiffness information and for quality control based on stiffness information measured over time will be described in further detail with reference to an example using a cultured cartilage originated from chondrocyte. In the present example, the stiffness of the cultured tissue was measured using a biosensor (available from AXIOM CO., LTD.).

Example 1

Preparation of Cultured Cartilage

Articular cartilage taken from the knee joint, hip joint and shoulder joint of a Japanese white tame rabbit, was subjected to an enzymatic treatment with a trypsin-EDTA solution and a collagenase solution to thereby separate and recover chondrocyte. The resulting chondrocytes were rinsed, followed by addition of a 10 v/v % FBS (fetal bovine serum)—DMEM (Dulbecco modified Eagle's minimum essential medium) to thereby prepare a cell suspension with a cell density of $1 \times 10^7$ cell/ml. One part by volume of the cell suspension was mixed with four parts by volume of a 3% Atelocollagen Implant (available from Koken Co., Ltd.), and 100 µl of the resulting mixture was mounted in a dome shape in a culture dish. The density of the seeded cells was $2 \times 10^6$ cell/ml.

The mounted mixture was gelatinized by allowing it to stand at 37° C. in a 5% $CO_2$ atmosphere for 0.5 to 1 hour, followed by addition of a medium and initiation of cultivation. The medium used herein was a 10 v/v % FBS-DMEM containing 50 µg/ml ascorbic acid and 100 µg/ml hyaluronic acid. The chondrocytes were thus incubated at 37° C. in a 5% $CO_2$ atmosphere for 3 weeks.

Measurement of Stiffness of Cultured Cartilage

The stiffness of the cultured cartilage prepared by the cultivation method were measured using the aforementioned stiffness measuring device 10. In this procedure, measuring element 22 was moved at a moving velocity of 2 mm/s and a travel of 2 mm.

Probe 20 was fixed to stand 12, and the computer was operated to set the moving velocity and travel. The cultured cartilage rinsed with PBS (phosphate buffered saline) was set with the dish at a measuring position and probe 20 was set at a predetermined distance from above the top of the cultured cartilage. The operator operated the computer to start the measurement, and measuring element 22 was driven by motor 30 and moved downward at the predetermined moving velocity. When measuring element 22 was moved downward the predetermined amount of travel, the rotation of motor 30 was reversed, and measuring element 22 was moved upward at the predetermined moving velocity to thereby complete the measurement of the stiffness. In this procedure, the travel of measuring element 22 driven by motor 30 was always being detected as a displacement from the reference position by the displacement sensor.

Displacement, pressure and tactile data were obtained during the series of downward-and-upward measuring processes, and the stiffness information of the cultured cartilage was then obtained from one or plurality of these data. The transplant compatibility of the cultured cartilage was examined based upon the obtained stiffness information.

Determination of Transplant Compatibility of Cultured Cartilage

Figure 2:
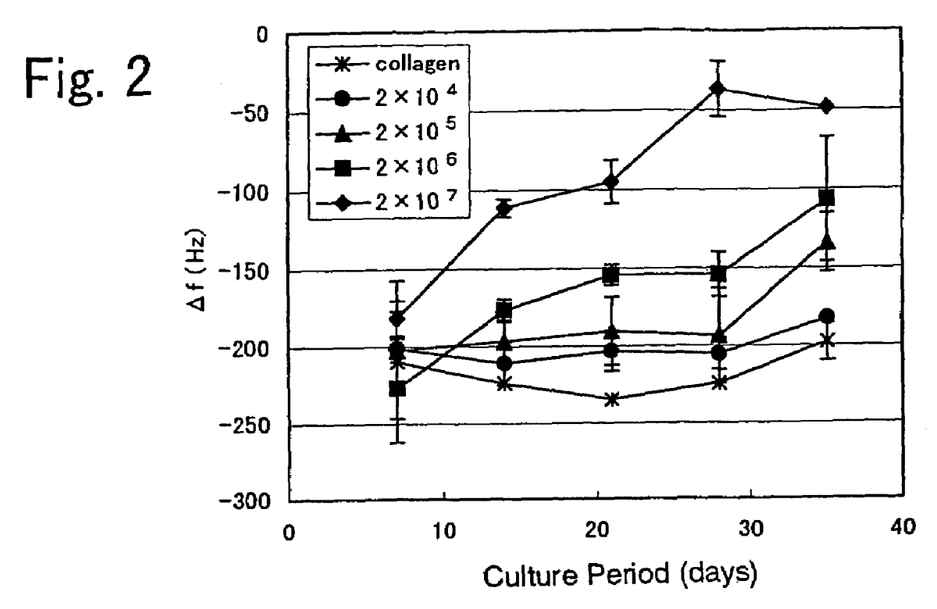
FIG. 2 is a graph showing a change in tactile information (the change in frequency $\Delta f$) with time at each seeding cell density in Example 1 according to the present invention.
Figure 3:
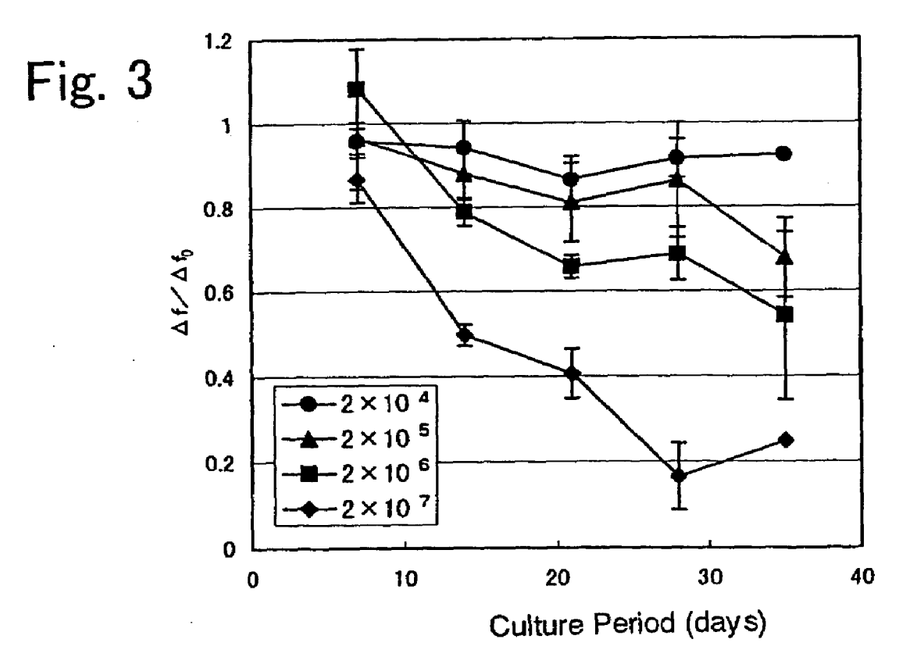
FIG. 3 is a graph showing a change in $\Delta f/\Delta f_0$ with time, which $\Delta f/\Delta f_0$ is normalized by dividing tactile information $\Delta f$ at each seeding cell density by tactile information $\Delta f_0$ of a collagen gel scaffold alone in Example 1.

FIG. 2 is a graph showing a change in tactile information (change in frequency $\Delta f$) with time at each seeding cell density when a predetermined displacement (1.5 mm downward from the top of the cultured tissue) was applied. FIG. 2 shows the data of a scaffold (collagen gel) without seeding of cells as a reference model. FIG. 3 is a graph showing a change in $\Delta f/\Delta f_0$ with time at each seeding cell density, in which the tactile information obtained in FIG. 2 at each seeding cell density was normalized by the tactile information of the collagen gel scaffold alone.

FIG. 2 shows that the stiffness increased with an increasing change in frequency $\Delta f$, and that the higher the seeding cell density was, the faster the stiffness increased. In contrast, cell growth affected the stiffness less at low seeding cell density. This is probably because a lower seeding cell density leads to a higher growth rate, and because of the influence of dedifferentiation, etc., the matrix production becomes less than that in a cultured tissue at a higher seeding cell density.

Generally, a cultured cartilage has sufficient compatibility as a cultured tissue for transplantation on or after 3 weeks (about day 21) from the beginning of cultivation. Accordingly, FIG. 2 shows that the change in frequency $\Delta f$ is preferably equal to or more than −200 Hz, and more preferably from −150 to 0 Hz in order to yield a transplant-compatible cultured tissue. FIG. 3 shows that $\Delta f/\Delta f_0$ is preferably from 0 to 0.9 and more preferably from 0 to 0.7 in order to yield a transplant-compatible cultured tissue.

Figure 4:
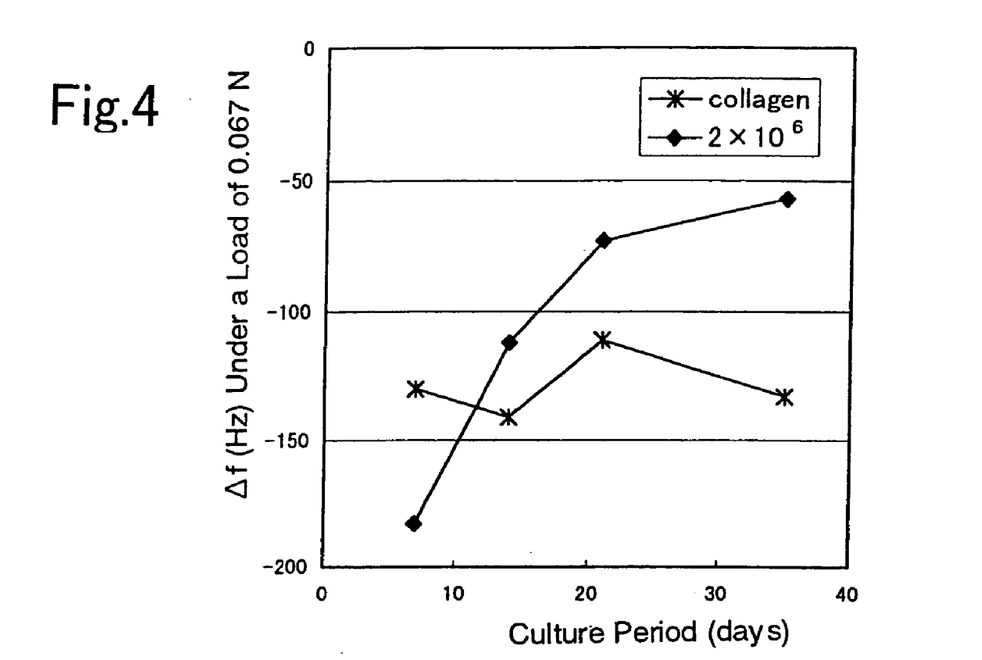
FIG. 4 is a diagram showing a change in frequency with time at a predetermined load in Example 1.

FIG. 4 is a graph showing a change with time of change in frequency $\Delta f$, when a predetermined load (0.067 N) was applied. In the figure, the results of a cultured tissue with an seeding cell density of $2\times10^6$ cell/ml and of a collagen gel scaffold alone are shown.

FIG. 4 shows that the change in frequency $\Delta f$, i.e., stiffness, under the predetermined load increased with the elapse of the culture period, as in the measurement at the predetermined displacement shown in FIGS. 2 and 3.

FIG. 4 also shows that the change in frequency $\Delta f$ under a load of 0.067 N is preferably equal to or more than −150 Hz and more preferably from −100 to 0 Hz in order to yield a transplant-compatible cultured tissue.

Figure 5:
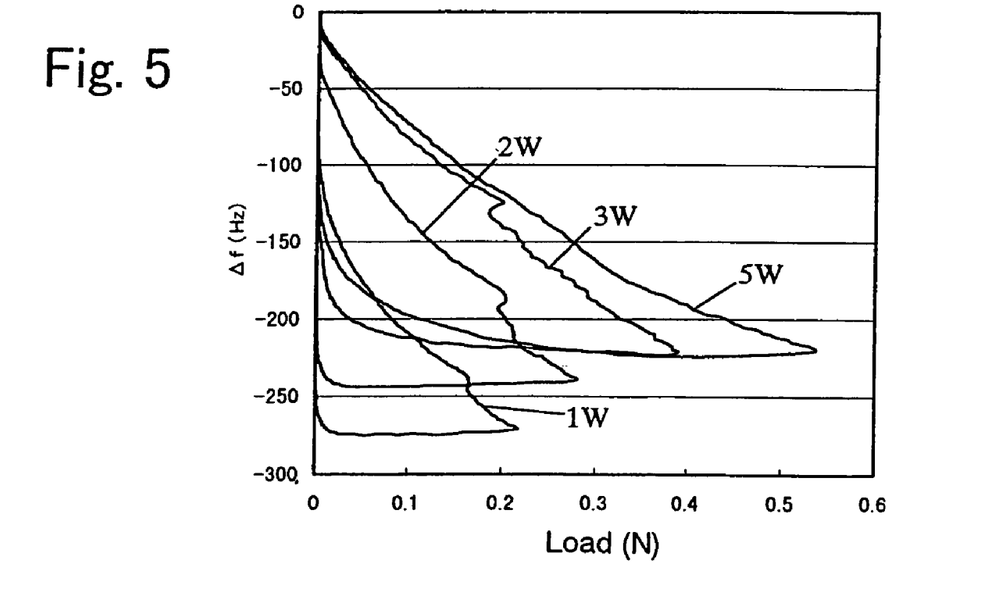
FIG. 5 is a diagram showing a relationship between the change in frequency and the load in Example 1.
Figure 6:
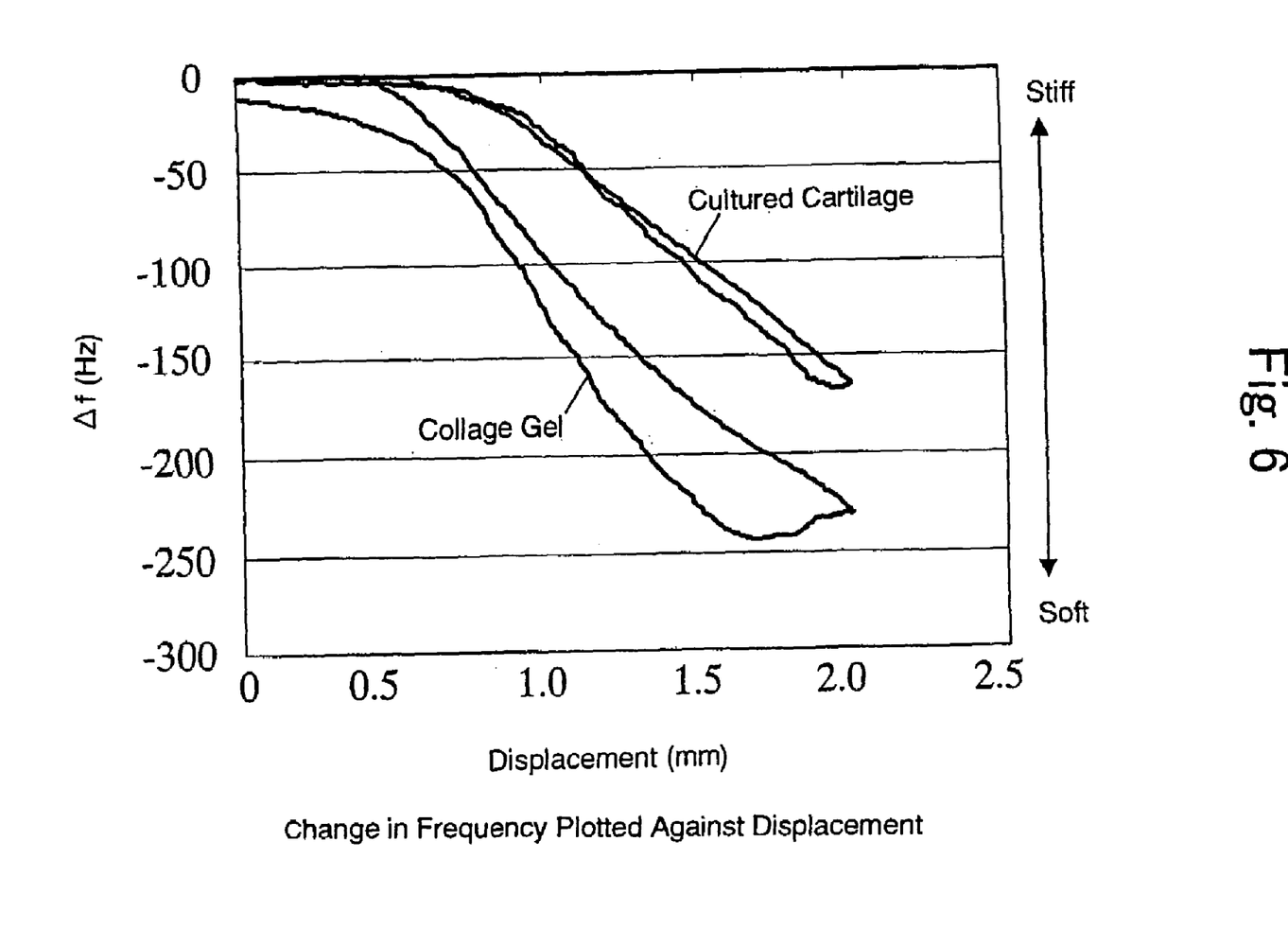
FIG. 6 is a diagram showing a relationship between the change in frequency and the displacement in Example 1.

FIG. 5 is a diagram showing the relationship of change in frequency with load (tactile sense—load diagram), and FIG. 6 is a diagram showing the relationship of change in frequency with displacement (tactile sense—displacement diagram). In the diagram of FIG. 5 showing the relationship between the change in frequency and load, the stiffness information can be obtained as a slope. In the figure, the symbols 1W, 2W, 3W and 5W respectively represent week 1, week 2, week 3 and week 5 of the cultivation. FIG. 5 shows that the slope was reduced with the elapse of the culture period, indicating that the stiffness of the cultured tissue increased. The slope under a predetermined load can be used as a criterion for the transplant compatibility. For example, the slope under a load from zero to 0.067 N is preferably from −1200 to 0 Hz/N and more preferably from −800 to −300 Hz/N.

In the tactile sense—load diagram, the elasticity information can be obtained as a difference between forward and return movements under a predetermined load. FIG. 5 shows that there was a great difference between the data of forward movement and of return movement (up-and-down movements of measuring element 22). This is probably because the movement of the cultured tissue to recover its shape cannot correspond to the return movement of measuring element 22, since the moving velocity of measuring element 22 is too high. The transplant compatibility of the cultured tissue based on its elasticity can be determined by setting an appropriate moving velocity of probe 20 in measurement or by decreasing the applied load.

The diagram of the change in frequency plotted against displacement in FIG. 6 shows a marked difference between forward and return movements. The difference between forward and return movements in the cultured cartilage was more remarkable than that in the collagen gel scaffold alone, indicating that the cultured cartilage became elastic.

As thus described, the tactile sense—load diagram or the tactile sense—displacement diagram can yield the change in frequency $\Delta f$ at a predetermined displacement or under a predetermined load, as well as the slope thereof and the elasticity information obtained from a difference between forward and return movements. Each of these parameters can be used alone or in combination as the criteria for the transplant characteristics. Accordingly, the use of the criteria obtained in the procedure can easily and properly determine the transplant compatibility of the cultured cartilage as prepared in the same manner.

Change in Stiffness with Time in Cultivation of Cultured Cartilage

All the graphs showing changes with time in FIGS. 2 to 4 and the relationship diagram in FIG. 5 show that the stiffness of the cultured cartilage including chondrocyte gradually increased with the elapse of the culture period whereas the stiffness of the collagen gel scaffold alone was almost even and did not change.

The stiffness of the cultured tissue was barely different from that of the reference model composed of collagen gel scaffold alone, until day seven (week one) of the culture, but there was a difference between the two in some seeding densities on or after day 14 (week two) of the cultivation. Even in a cultured cartilage with a low seeding cell density, which exhibited less difference in stiffness from the collagen gel scaffold alone, the cells at this point of time were found to have proliferated, when a cross-section was prepared from the cultured tissue at this point of time and its chromatic figure was observed. On day 21 (week three) of the cultivation, the cultures exhibited clear differences in stiffness from the collagen gel scaffold alone, and also exhibited greater differences in stiffness with each other due to difference in seeding cell density. The stiffness of the cultured tissue with an seeding cell density of $2\times10^7$ cell/ml did not significantly change on or after day 21 of the cultivation.

Quality Control Based on Data on Change with Time

The cultured cartilage in the present example showed no change in stiffness immediately after the initiation of cultivation, but showed remarkable changes in stiffness from day 14 to day 21 of the cultivation, as shown in FIGS. 2 to 4. The transplant compatibility of the cultured cartilage was predicted based on the above change in stiffness with time to thereby appropriately change culture conditions such as seeding cell density and culture medium composition. By changing culture conditions, the degree of change in stiffness and degree of cell growth can be changed to thereby control the cultivation so that the cultured tissue has an appropriate stiffness as a cultured tissue for transplantation after a desired culture period and to thereby stably provide a cultured tissue having an appropriate stiffness.

Example 2

Example 2 according to the present invention will be described with reference to FIGS. 7 and 8. In Example 2, part of the aforementioned measuring model and of the measurement conditions in Example 1 were changed. Specifically, a dome shaped cultured cartilage 2.8–3.0 cm in diameter and 3 mm in thickness was subjected to measurement by using probe 20 having a 1 mm diam. semispherical contact 32 in this example. Stiffness measuring device 10 used in this example was the same as that used in the measuring model and in Example 1, except for the size of contact 32.

Initially, a cultured cartilage was prepared in the same manner as in Example 1, except that a cell suspension with a cell density of $1 \times 10^7$ cell/ml was mixed with a 3% atelocollagen solution, and 1500 μl (seeding cell density: $2 \times 10^6$ cell/ml) was mounted in a dome shape in a culture dish.

The stiffness of the cultured cartilage was measured at a total of 30 points including the top of the cultured cartilage and the other 29 points. Upon measurement, measuring element 22 was moved at a moving velocity of 2 mm/s and a travel of 2 mm. The density of the points of measurement was about five per 1 $cm^2$ of the surface of the cultured cartilage. The other measuring conditions were the same as in the measuring model and in Example 1.

Figure 7:
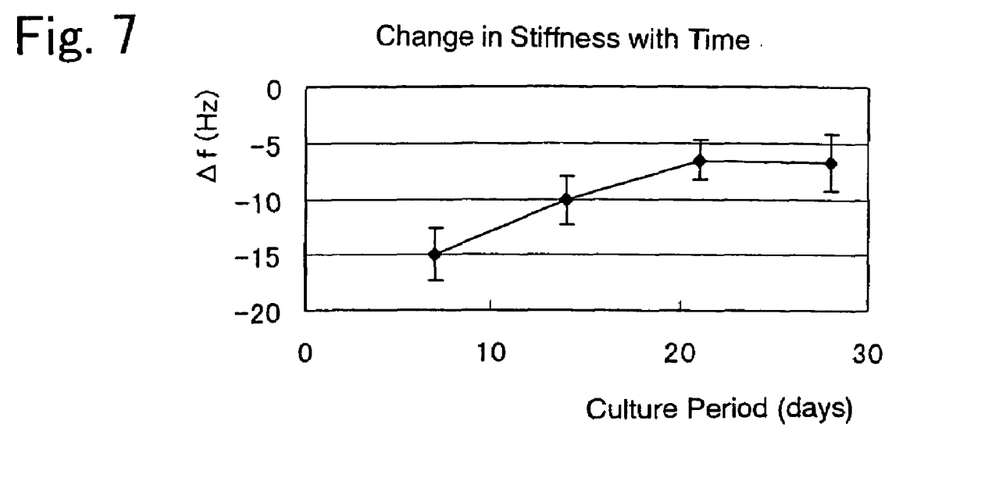
FIG. 7 is another graph showing a change in tactile information (the change in frequency $\Delta f$) with time in Example 2 according to the present invention.

FIG. 7 is a graph showing a change in tactile information (the change in frequency Δf) with time under a predetermined load ($4.9 \times 10^{-3}$ N (0.5 gf)). The graph shows the average of the measurements at the 30 points. FIG. 7 shows that the change in frequency Δf under the predetermined load varied in a manner similar to Example 1and that the stiffness of the cultured cartilage increased with elapsed time of the culture period. It also shows that with the determination of the stiffness based on the average of plural measurements the change in stiffness of the cultured cartilage can be reliably grasped and is suitable for precise measurement and for the determination of transplant compatibility. Under the measuring conditions in the present example, the transparent compatibility of the cultured cartilage can be determined, the quality of the cultured cartilage can be controlled, and an appropriate cultured cartilage can be prepared with an appropriate range for transplant compatibility in terms of change in frequency Δf of preferably from −15 to 0 Hz, and more preferably from −10 to 0 Hz.

Figure 8:
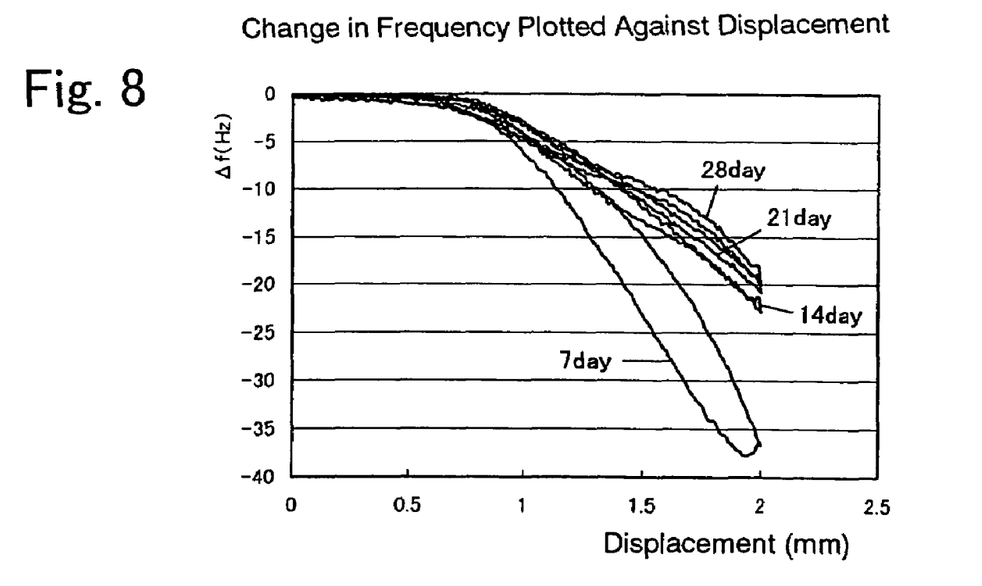
FIG. 8 is a diagram showing a relationship between the change in frequency and the displacement in Example 2.

FIG. 8 is a diagram showing the relationship of change in frequency with displacement (tactile sense—displacement diagram). FIG. 8 shows that the change in frequency Δf with respect to increasing displacement increased with elapsed time of the culture period as in Example 1, indicating that the stiffness of the cultured cartilage increased. It also shows a difference in the tactile information between forward movement (downward movement of the contact) and return movement (upward movement of the contact) on day seven, indicating that the cultured tissue had not yet had sufficient elasticity. On or after day fourteen, there was almost no difference between forward and return movements, indicating that the cultured tissue had sufficient elasticity and returned to its original state following the upward movement of the contact. In FIG. 8, the travel of measuring element 22 from the reference position is defined as the displacement. Consequently, contact 32 came in contact with the cultured cartilage at a travel of 0.5 mm.

As thus described, the state of cell growth, i.e., the state of cultivation in the cultured cartilage is measured as the stiffness information according to the present invention, and the transplant compatibility of the cultured tissue can be nondestructively and concretely determined. The measurement and prediction of a change with time can control the quality of the cultured tissue to yield a cultured tissue with stable quality for transplantation. Additionally, by carrying out this quality control transplant-compatible cultured tissue can be systematically prepared efficiently.

The present invention has been illustrated herein by taking cultured cartilage as an example, but it is obvious to those skilled in the art that the present invention can also be applied to any cultured tissues in which the transplant compatibility can be determined based on stiffness information thereof. In such cases, the stiffness information can be obtained in the same manner as above using a cell types constituting the cultured tissue in question.

Stiffness measuring device 10 used in the present embodiment includes pressure sensor unit 26 and displacement sensor unit 28 in addition to tactile sensor unit 24. However, stiffness measuring device 10 only needs to include tactile sensor unit 24 alone, for the purpose of measuring the stiffness of the cultured tissue to thereby determine its transplant compatibility. With this configuration the transplant compatibility of the cultured tissue can be determined using a simpler device.

In stiffness measuring device 10 used in the present embodiment, probe 20 is fixed to stand 12 via arm 14 and supporting shaft 16, but probe 20 need not be fixed as long as it can come in contact with the cultured tissue under a certain load. For example, the present invention can also be applied to measurement of stiffness of cultured tissue using a pen type stiffness measuring device with similar functions.

As described above, with the present invention the stiffness of a cultured tissue can be nondestructively measured and the transplant compatibility thereof can be easily determine, the quality of the cultured tissue can be easily and appropriately controlled, and a transplant-compatible cultured tissue can be reliably and easily prepared.

Other embodiments and variations will be obvious to those skilled in the art, and this invention is not to be limited to the specific matters stated above.

What is claimed is:

1. A method for obtaining a desired stiffness of cultured tissues and optimizing transplant compatibility of said cultured tissues, said method comprising the steps of:

determining a desired stiffness of a cultured tissue based on a previously defined reference model;

measuring a stiffness of an in vitro cultured tissue at a predetermined time after an initiation of culture to obtain a measurement of stiffness;

predicting a change in the stiffness of said cultured tissue over time by comparing the measurement of stiffness of said cultured tissue to the previously defined reference model, to obtain a prediction of the change in stiffness over time; and controlling a set of culture conditions for said cultured tissue based on the prediction of the change in stiffness, in order to achieve the desired stiffness.

2. The method according to claim 1, further comprising:

measuring the stiffness of said cultured tissue using a stiffness measuring device, said stiffness measuring device comprising a detecting unit and a calculation means, said detecting unit including a contact unit, a vibrator connected to said contact unit, and a vibration detecting unit for detecting a vibration of said vibrator; and determining stiffness information using said calculation means to obtain a calculation based on a detected result from said vibration detecting unit.

3. The method according to claim 2, wherein the contact unit of the stiffness measuring device contacts and measures an area of the cultured tissue that is one fifth or less of an entire area of the cultured tissue, a measurement of stiffness is obtained for 5 to 50 areas per cultured tissue, and the set of culture conditions is controlled based on an average of the 5 to 50 measurements of stiffness.

4. The method according to claim 2, wherein the contact unit of the stiffness measuring device contacts an area of the cultured tissue that ranges from an area equal to approximately one fifth of the entire area of the cultured tissue to an area equal to the entire area of the cultured tissue, and the set of culture conditions is controlled based on a resultant measurement of stiffness of said area obtained through use of said stiffness measuring device.

5. A method of obtaining a desired stiffness of cultured tissues and optimizing transplant compatibility of said cultured tissues comprising the steps of:
    determining a desired stiffness of a cultured tissue based on a previously defined reference model;
    measuring a stiffness of an in vitro cultured tissue at a predetermined time after a commencement of a culture period of said cultured tissue to obtain a measurement of stiffness;
    comparing the measurement of stiffness of said cultured tissue to that of the previously defined reference model; and
    determining a transplant compatibility of the cultured tissue based upon a resulting comparison of the measurement of stiffness of said cultured tissue to the previously defined reference model, the stiffness of said cultured tissue being an indicator of the transplant compatibility of said cultured tissue;
    predicting a change in stiffness of said cultured tissue over time, to obtain a prediction of the change in stiffness over time, based on the comparison of the measurement of stiffness of said cultured tissue with that of the previously defined reference model; and
    controlling a set of culture conditions of said cultured tissue based upon the predicted change in stiffness of said cultured tissue to thereby prepare a transplant-compatible cultured tissue having the desired stiffness, the stiffness of said cultured tissue being an indicator of transplant compatibility.

6. A method of determining transplant compatibility comprising the steps of:
    determining a desired stiffness of a cultured tissue based on a previously defined reference model;
    measuring a stiffness of said cultured tissue immediately upon a commencement of a culture period for said cultured tissue, to obtain a measurement of stiffness;
    measuring stiffness of said cultured tissue at a predetermined time after the commencement of the culture period to obtain another measurement of stiffness;
    determining a change in the stiffness of the cultured tissue between the commencement of the culture period and the predetermined time; and
    determining a transplant compatibility of the cultured tissue based on the change in stiffness, the stiffness of said cultured tissue being an indicator of the transplant compatibility of said cultured tissue.

* * * * *